United States Patent
Skubitz et al.

(10) Patent No.: US 10,149,693 B2
(45) Date of Patent: Dec. 11, 2018

(54) LEAD INSERTION TOOL

(71) Applicant: MEDTRONIC, INC., Minneapolis, MN (US)

(72) Inventors: Sean P. Skubitz, Forest Lake, MN (US); Phillip C. Falkner, Minneapolis, MN (US); William Ferris, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 197 days.

(21) Appl. No.: 14/621,590

(22) Filed: Feb. 13, 2015

(65) Prior Publication Data
US 2015/0230813 A1 Aug. 20, 2015

Related U.S. Application Data

(60) Provisional application No. 61/939,821, filed on Feb. 14, 2014.

(51) Int. Cl.
*A61B 17/28* (2006.01)
*A61N 1/05* (2006.01)

(52) U.S. Cl.
CPC .......... *A61B 17/282* (2013.01); *A61N 1/0553* (2013.01)

(58) Field of Classification Search
CPC .............. A61B 17/282; A61B 17/2804; A61B 18/1442
USPC ......................................... 606/210
See application file for complete search history.

(56) References Cited

U.S. PATENT DOCUMENTS

| | | | | |
|---|---|---|---|---|
| 5,334,215 A * | 8/1994 | Chen | ...................... | A61B 17/30 294/99.2 |
| 5,569,300 A * | 10/1996 | Redmon | ............ | A61B 17/0206 600/219 |
| 5,693,057 A * | 12/1997 | Dusek | ................... | A61F 2/1664 606/107 |
| 6,648,902 B2 * | 11/2003 | Colgan | ................... | A61B 17/28 600/218 |
| 7,455,639 B2 * | 11/2008 | Ritland | ................... | A61B 17/02 600/201 |
| 2002/0094507 A1 * | 7/2002 | Feuer | ..................... | A61B 17/30 433/162 |
| 2005/0070955 A1 * | 3/2005 | Young | .................... | A61B 17/30 606/210 |
| 2006/0173522 A1 | 8/2006 | Osorio | | |
| 2007/0078503 A1 | 4/2007 | Kuzma et al. | | |
| 2008/0200923 A1 * | 8/2008 | Beckman | ............ | A61F 9/00781 606/108 |
| 2009/0024123 A1 * | 1/2009 | Young | ................... | A61B 17/30 606/41 |

(Continued)

OTHER PUBLICATIONS

PCT Patent Application No. PCT/US2015/015740, filed Feb. 13, 2015; International Search Report / Written Opinion dated May 4, 2015; 10 pages.

*Primary Examiner* — Julie A Szpira
(74) *Attorney, Agent, or Firm* — Mueting, Raasch & Gebhardt, P.A.

(57) ABSTRACT

A lead insertion tool includes a first leg having a first rail element pivotally coupled to the first leg distal end and a second leg having a second rail element pivotally coupled to the second leg distal end. The first rail element and the second rail element are configured to receive a lead. Medical kits and methods of using the same are also disclosed.

20 Claims, 7 Drawing Sheets

(56) References Cited

U.S. PATENT DOCUMENTS

2012/0283744 A1\* 11/2012 Slavin .................... A61B 17/30
  606/129
2014/0379014 A1\* 12/2014 Abri ................... A61B 17/2804
  606/170

\* cited by examiner

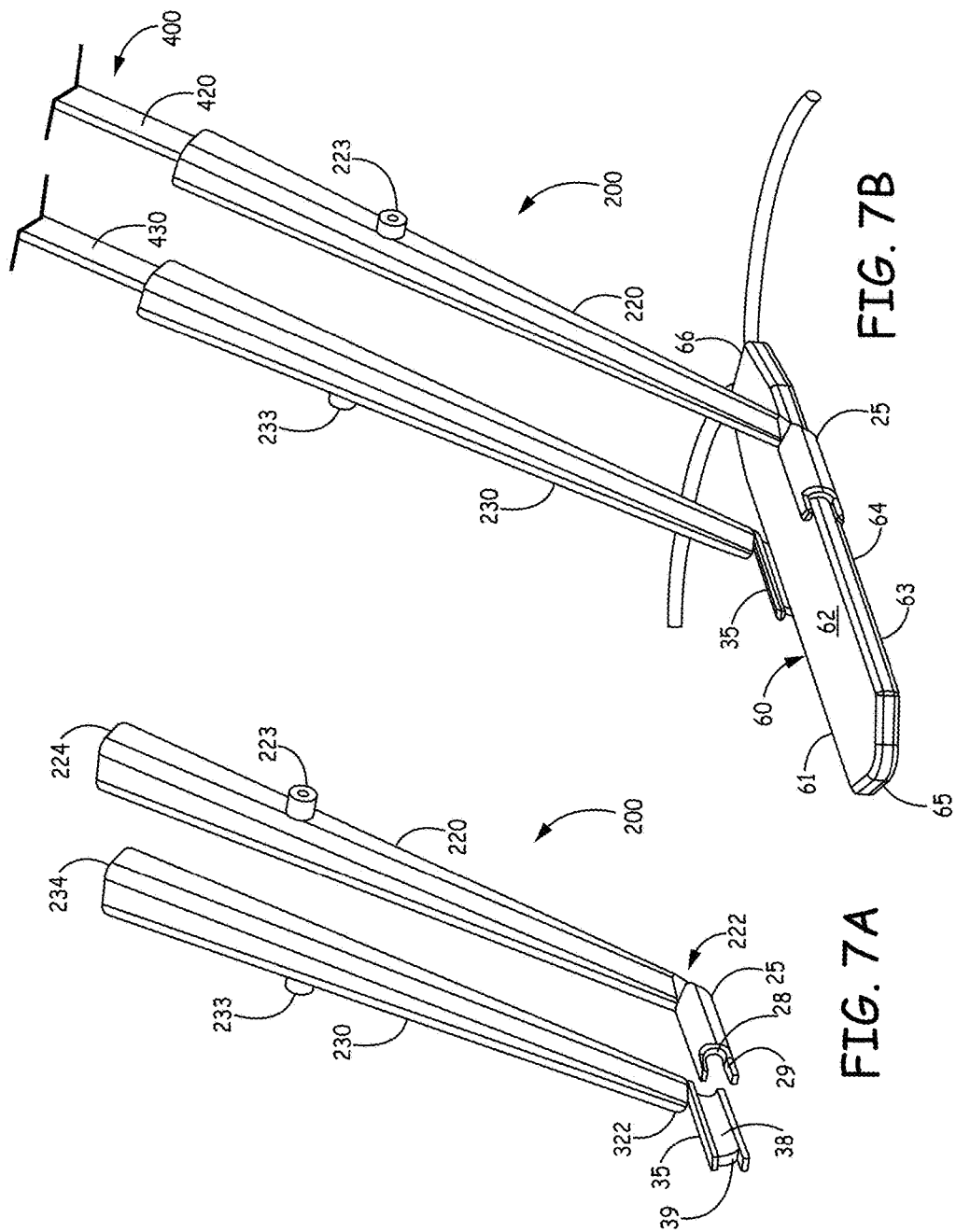

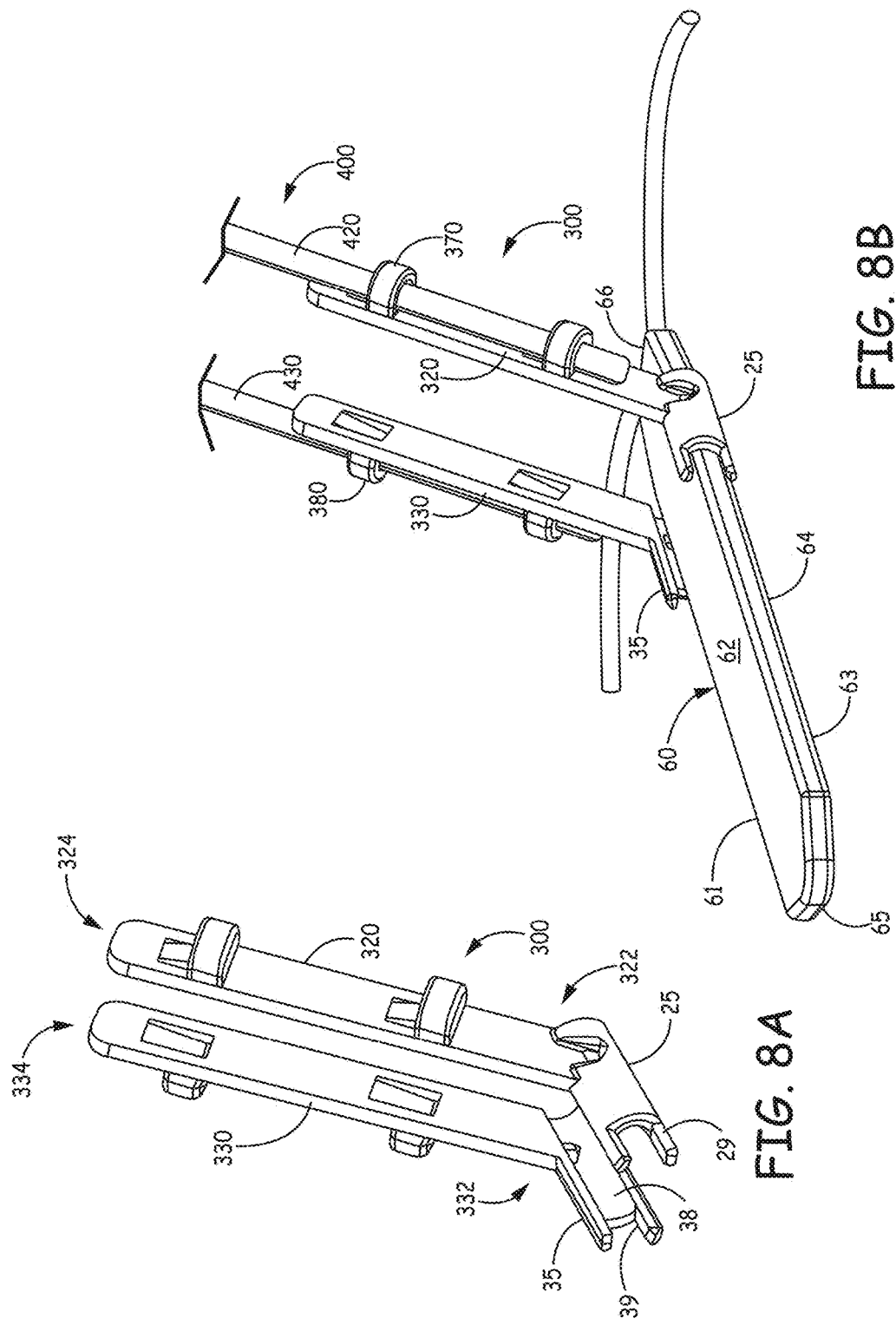

LEAD INSERTION TOOL

PRIORITY APPLICATION

This application claims priority to U.S. Provisional Application No. 61/939,821, filed on Feb. 14, 2014, and entitled "LEAD INSERTION TOOL". The entire disclosure is incorporated herein by reference.

BACKGROUND

Placing surgical leads midline or other target area can be challenging due to the type of procedure, such as lateral, midline laminectomy/lamonotmy approaches, and others using less invasive dilation/retraction type tools. Placing the lead is typically done with forceps. Standard forceps provide little ability to steer the lead because it enables only two points of contact. As a result, holding the lead on side surfaces can cause rotation and holding the lead along the lateral edges provides little ability securely hold the lead because the thin and flexible nature of the lead can cause it to flip within the blades of the forceps as pressure on the forceps is increased.

The electrode used in spinal cord stimulation typically resembles a paddle that is generally rectangular when viewed from above. To insert and advance this paddle-type electrode, surgeons typically use straight or bayonet-type forceps as described above. Surgeons must suitably grip the edges of the electrode to ensure its stability. An excessive gripping force, however, tends to bend the electrode in a slight U-shape. A bent electrode can hinder insertion of the electrode. Thus, there has developed a need for a tool that can make inserting a paddle-type electrode in laminectomy efficient and surgeon-friendly.

SUMMARY

The present disclosure relates to lead insertion tools that place paddle leads efficiently within the target area. The lead insertion tool can be a unitary device where the opposing gripping rails are pivotally coupled to parallel extending legs or the lead insertion tool can be gripping rails that are disposed onto conventional forceps. These lead insertion tools can place and push the paddle lead into the target location efficiently.

In one illustrative embodiment, a lead insertion tool includes parallel extending legs. The first leg has a first leg distal end and an opposing first leg proximal end. A first rail element is pivotally coupled to the first leg distal end. The second leg has a second leg distal end and an opposing second leg proximal end. A second rail element is pivotally coupled to the second leg distal end. The first rail element and the second rail element are configured to receive a lead.

In another illustrative embodiment, a lead insertion tool kit includes a first leg having a first leg distal end and an opposing first leg proximal end. A first rail element is coupled to the distal leg end and forming an angle. A second leg having a second leg distal end and an opposing second leg proximal end and parallel extending with the first leg. A second rail element is coupled to the second leg distal end and forming an angle. The first rail element and the second rail element are configured to receive a lead. The first leg is not coupled to the second leg.

In a further embodiment, a medical kit includes a lead insertion tool as described herein and a paddle lead that is configured to be received by the lead insertion tool.

In a further embodiment, a method includes gripping a paddle lead along opposing lateral edges with opposing rail elements of a lead insertion tool. The opposing rails form an angle with the first and second legs of the lead insertion tool. The opposing rails have a slot extending into a distal end of each rail. Then the method includes placing the paddle lead into an initial target area, releasing the paddle lead from the lead insertion tool, contacting the rail elements together to form a slot configured to receive the paddle lead, engaging a proximal end of the paddle lead into the slot, and pushing the paddle lead into a second target area with the lead insertion tool.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which:

FIG. 7A is a perspective view of another illustrative lead insertion tool that can be secured to forceps;

FIG. 7B is a perspective view of an illustrative lead insertion tool of FIG. 7A gripping a paddle lead;

FIG. 8A is a perspective view of another illustrative lead insertion tool that can be secured to forceps; and FIG. 8B is a perspective view of an illustrative lead insertion tool of FIG. 8A gripping a paddle lead.

DETAILED DESCRIPTION

Figure 1:
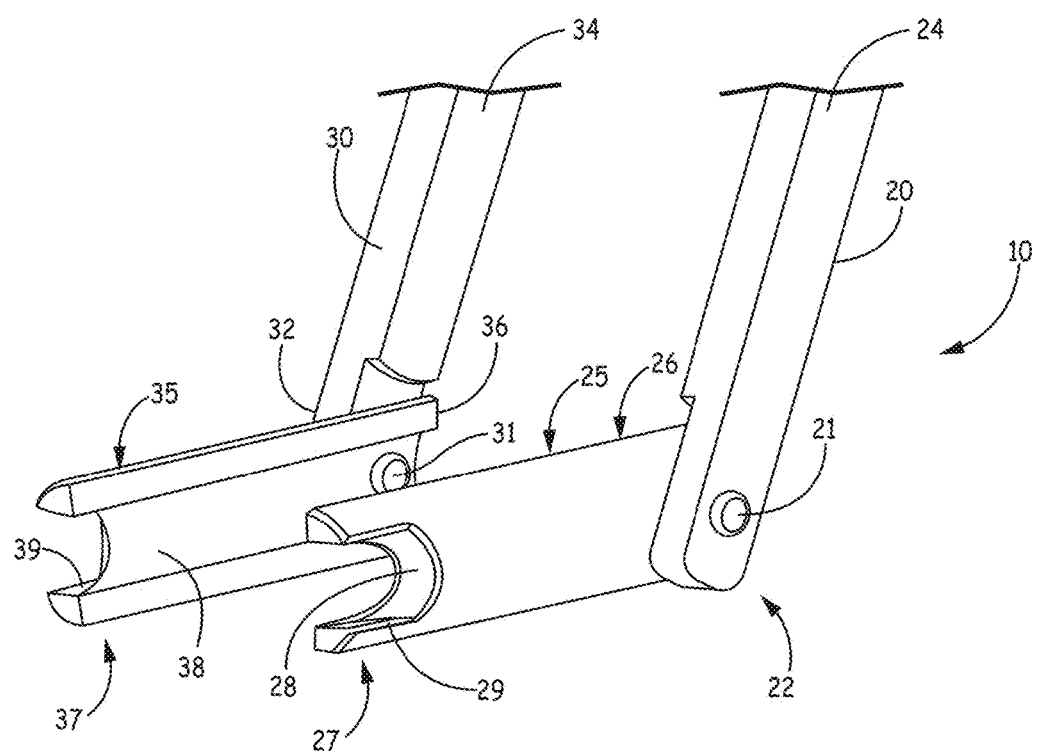
FIG. 1 is a perspective view of an illustrative distal end of a lead insertion tool.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range. As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The term "coupled" refers to two elements being attached to each other either directly (in direct contact with each other) or indirectly (having one or more elements between and attaching the two elements).

The present disclosure relates to lead insertion tools that can place paddle leads efficiently within the target area. The lead insertion tool can be a unitary device where the opposing gripping rails are pivotally coupled to parallel extending legs or the lead insertion tool can be gripping rails that are disposed onto conventional forceps. These lead insertion tools can place and push the paddle lead into the target location efficiently. In many embodiments the length of each leg can be independently adjusted. In many embodiments the angle of each rail relative to the attached leg can be independently adjusted. In some embodiments, the angle of each rail relative to the attached leg is fixed. In some embodiments the lead insertion tool is a unitary article where the legs are joined at a proximal end. In other embodiments the lead insertion tool is two leg elements that can be coupled to forceps and can be disposable once used. While the present disclosure is not so limited, an appreciation of various aspects of the disclosure will be gained through a discussion of the examples provided below.

Figure 2:
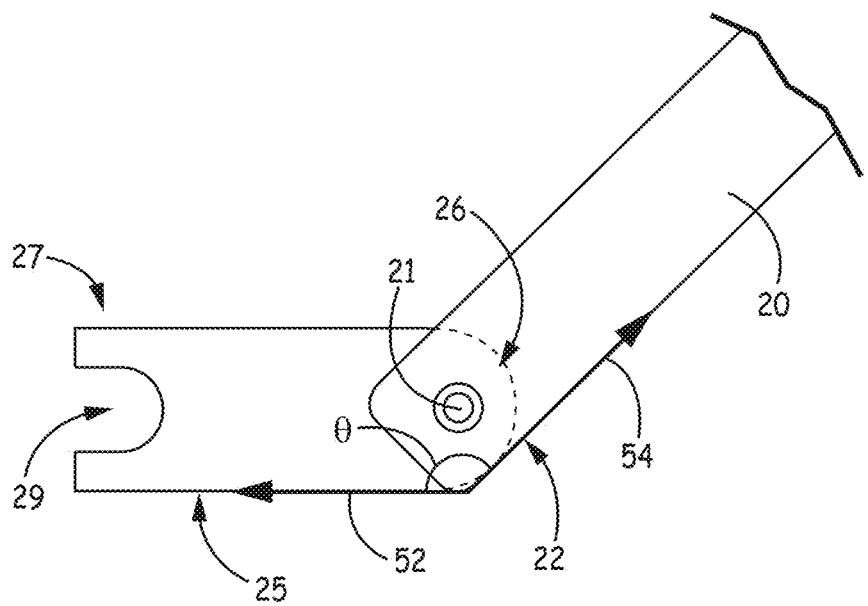
FIG. 2 is a schematic side view of the lead insertion tool of FIG. 1.
Figure 3:
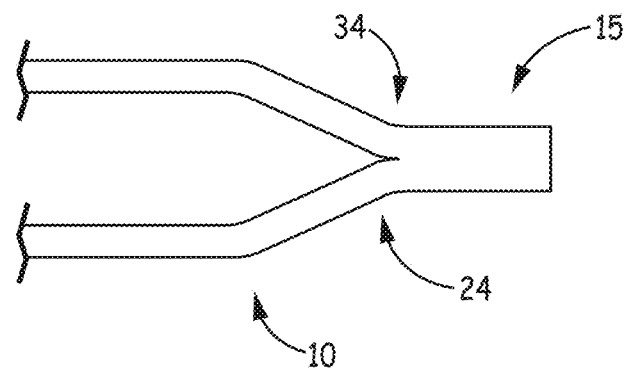
FIG. 3 is a schematic front view of an illustrative proximal portion of the lead insertion tool illustrative the first and second legs being coupled.

FIG. 1 is a perspective view of an illustrative distal end of a lead insertion tool 10. FIG. 2 is a schematic side view of the lead insertion tool 10 of FIG. 1. FIG. 3 is a schematic front view of an illustrative proximal portion of the lead insertion tool 10 illustrative the first 20 and second legs 30 coupled at the proximal end 15 of the lead insertion tool 10. The features described in FIG. 1-3 can be independently utilized in any of the embodiments described in FIG. 4-8B. For example, even though FIG. 7A and FIG. 8A illustrate rails 25, 35 being rigidly fixed to the legs 20, 30, it is understood that these rails 25, 35 can be pivotally coupled to the legs 20, 30 as illustrated in FIG. 1-3.

In many embodiments the lead insertion tool 10 includes a first leg 20 having a first leg distal end 22 and an opposing first leg proximal end 24. A first rail element 25 is pivotally coupled, by a pivot pin 21 for example, to the first leg distal end 22. A second leg 30 has a second leg distal end 32 and an opposing second leg proximal end 34. The second leg 30 can be parallel extending with the first leg 20. A second rail element 35 is pivotally coupled, by a pivot pin 31 for example, to the second leg distal end 32. The first rail element 25 and the second rail element 35 are configured to receive a lead and can include a channel 28, 38 that can mate with and receive a surface of a lead body, such as a paddle lead.

In many embodiments the first rail element 25 pivots relative to the first leg 20 and forms an angle θ defined by a bottom surface 52 of the first rail element 25 and a bottom surface 54 of the first leg 20. The first rail element 25 can be pivoted to form any useful angle θ, such as 90 to 180 degrees, or from 100 to 175 degrees, or from 110 to 170 degrees. In some embodiments, the intersection of the first rail element 25 and the first leg 20 includes detent elements that create a plurality of pre-set angles θ. In many embodiments the proximal end 26 or bottom surface 52 of the first rail element 25 and the first leg distal end 22 or bottom surface 54 of the first leg 20 forms a smooth angle. A smooth angle refers to no surface extending beyond the angle planes. For example, no portion of the rail 25 intersects the bottom surface 54 of the first leg 20 and no portion of the leg 20 intersects the bottom surface 52 of the first rail element 25. This can be helpful in minimizing surfaces that can catch tissue during a procedure using the disclosed lead insertion tool 10.

In some embodiments the first leg 20 is coupled to the second leg 30 at the first leg proximal end 24 and second leg proximal end 34. This is illustrated in FIG. 3. In these embodiments the lead insertion tool 10 is a unitary article where the legs 20, 30 are joined at a proximal end 15 of the lead insertion tool 10. In other embodiments the first leg 20 is not coupled to the second leg 30 and these legs 20, 30 are instead fixed to the opposing legs of a forceps device.

Figure 5:
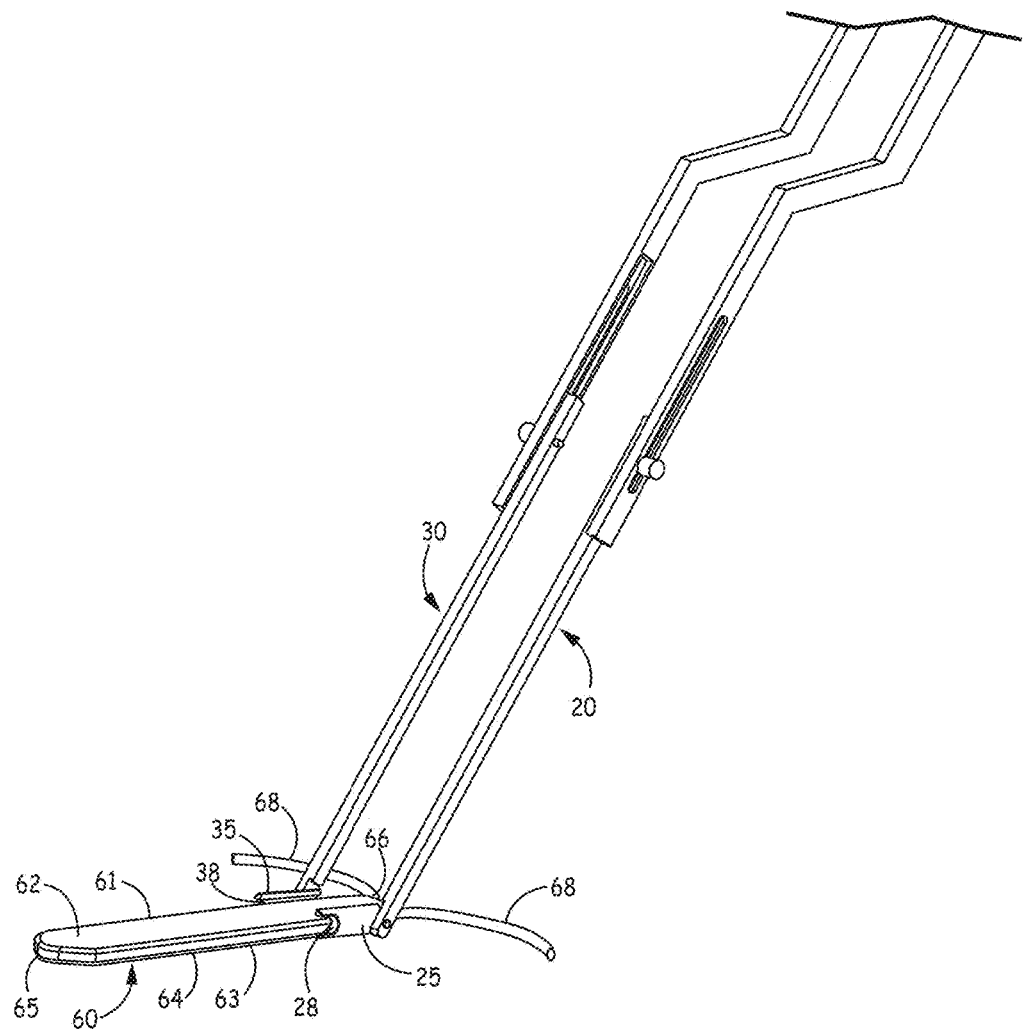
FIG. 5 is a perspective view of an illustrative lead insertion tool of FIG. 4 gripping a paddle lead.

The first rail element 25 has a rail distal end 27 and an opposing rail proximal end 26 defining a rail lateral length. The first rail element 20 is coupled to the first leg distal end 22 and in many embodiments the first rail 25 is pivotally coupled to the first leg distal end 22. The first rail element 20 can include a channel 28 that extends along its length. The channel 28 can be configured to mate with and receive a surface of a lead. For example, the channel 28 can be configured to mate with and receive a side surface of a paddle lead as illustrated in FIG. 5 to locate the lead in a target area.

Figure 6:
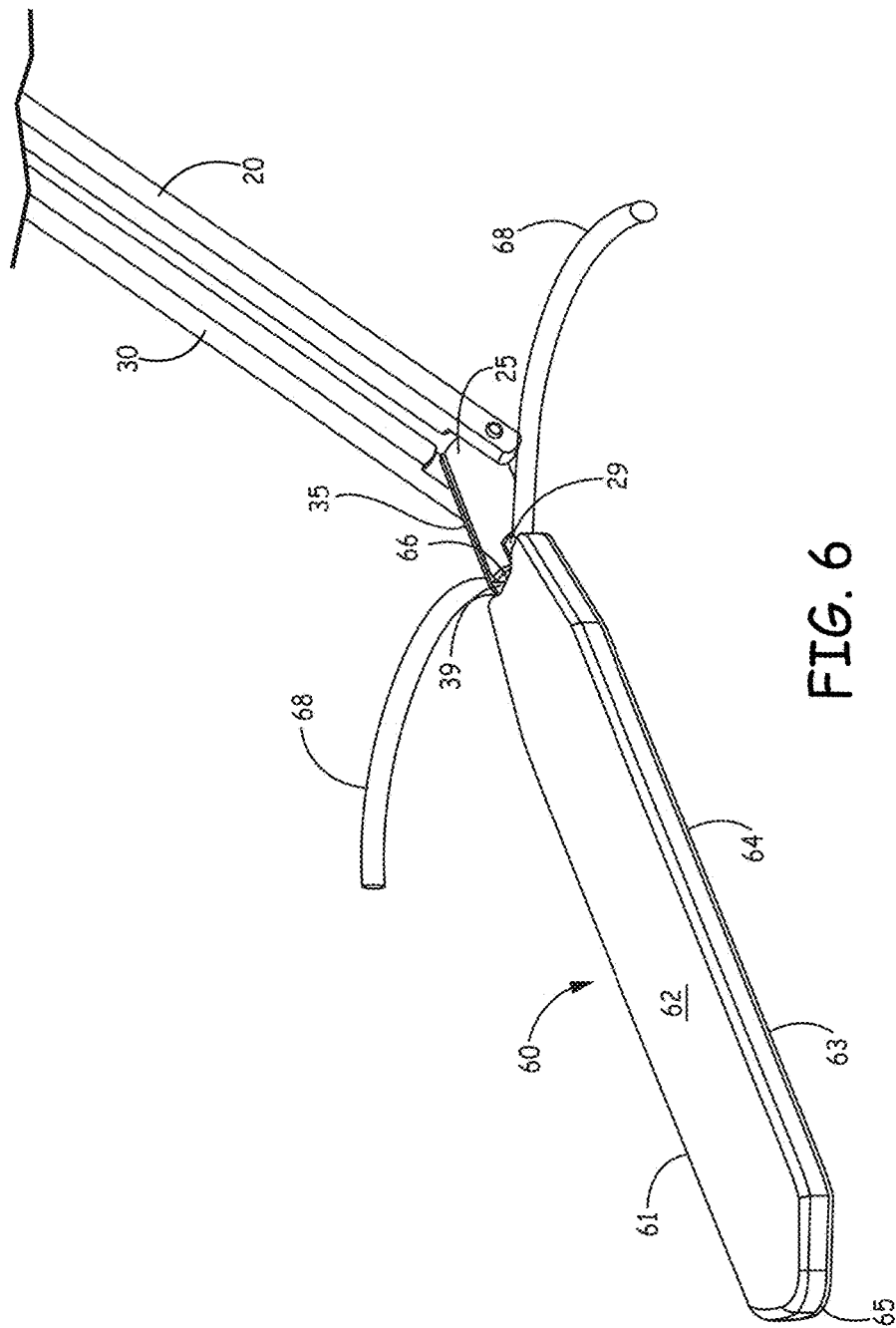
FIG. 6 is a perspective view of an illustrative lead insertion tool of FIG. 4 mated to a rear portion of the paddle lead for pushing the paddle lead.

The rail distal end 27 can include a slot 29 configured to receive a lead, especially when the first and second rails 25, 35 are in contact with each other. The slot 29 extends into the rail distal end 27. In many embodiments the slot 29 is coextensive with the channel 28 and extends along a length of the first rail 25. The slot 29 can be configured to mate with and receive a surface of a lead. For example, the slot 29 can be configured to mate with and receive an end surface of a paddle lead as illustrated in FIG. 6 to push the lead into a final target area.

The second rail element 35 has a rail distal end 37 and an opposing rail proximal end 36 defining a rail lateral length. The second rail element 30 is coupled to the second leg distal end 32 and in many embodiments the second rail 35 is pivotally coupled to the second leg distal end 32. The second rail element 30 can include a channel 38 that extends along its length. The channel 38 can be configured to mate with and receive a surface of a lead. For example, the channel 38 can be configured to mate with and receive a side surface of a paddle lead as illustrated in FIG. 5 to locate the lead in a target area.

The rail distal end 37 can include a slot 39 configured to receive a lead, especially when the first and second rails 25, 35 are in contact with each other. The slot 39 extends into the rail distal end 37. In many embodiments the slot 39 is coextensive with the channel 38 and extends along a length of the second rail 35. The two slots 29 and 39 can mate with each other to receive the lead when the first and second rails 25, 35 are in contact with each other. The slot 39 can be configured to mate with and receive a surface of a lead. For example, the slot 39 can be configured to mate with and receive an end surface of a paddle lead as illustrated in FIG. 6 to push the lead into a final target area.

Figure 4:
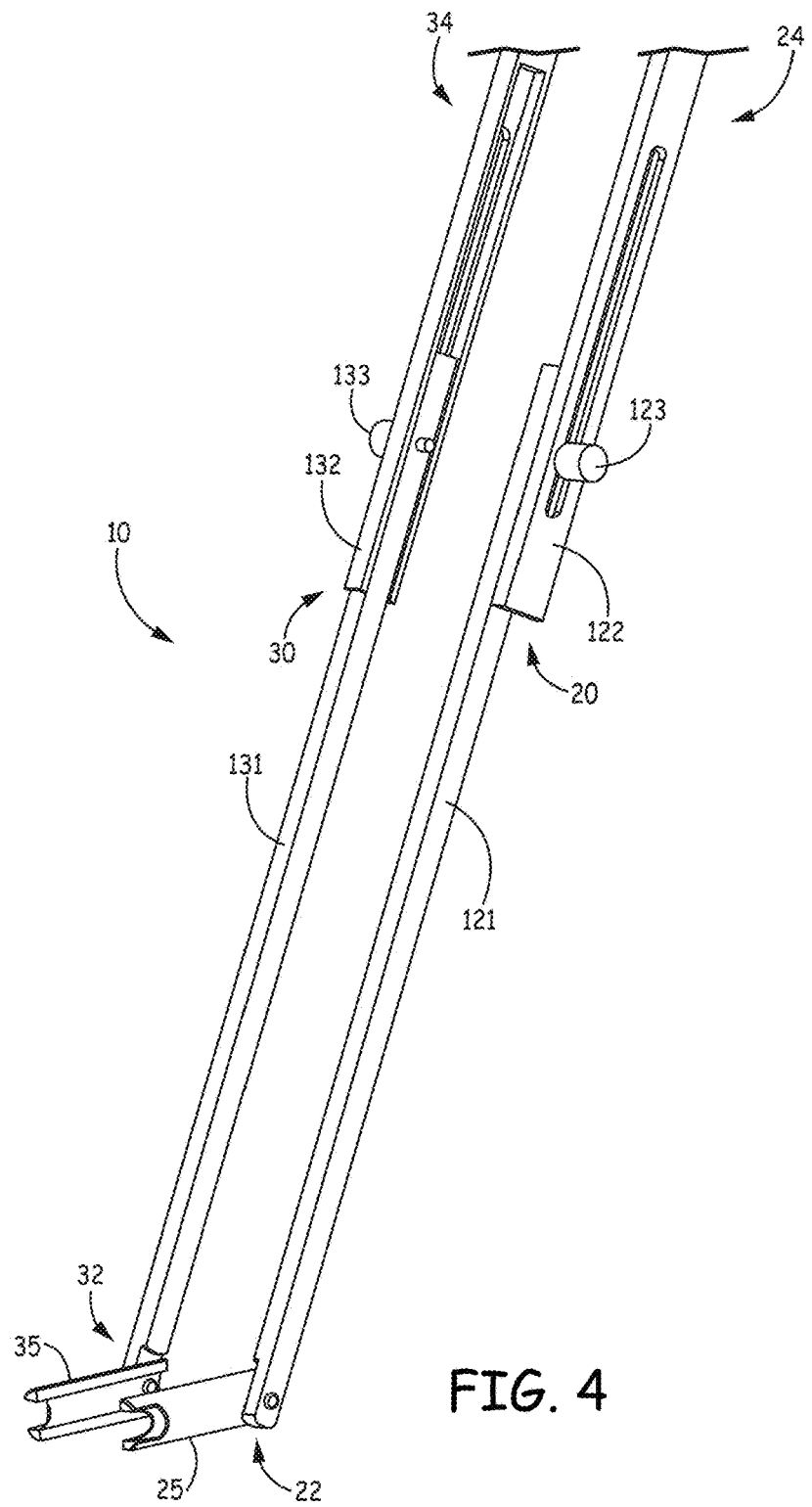
FIG. 4 is a perspective view of an illustrative lead insertion tool having adjustable length legs.

FIG. 4 is a perspective view of an illustrative lead insertion tool 10 having adjustable length legs. The first leg 20 and the second leg 30 may or may not be coupled to each other as described herein. The first leg 20 includes a first leg portion 121 and a second leg portion 122 being slide-able relative to the first leg portion 121. In the illustrated embodiment, a set screw 123 can be utilized to fix the relative positions of the first leg portion 121 and a second leg portion 122.

The second leg 30 includes a first leg portion 131 and a second leg portion 132 being slide-able relative to the first leg portion 131. In the illustrated embodiment, a set screw 133 can be utilized to fix the relative positions of the first leg portion 131 and a second leg portion 132. The first leg 20 has a first leg length extending between the first leg distal end 22 and the first leg proximal end 24. The second leg 30 has a second leg length extending between the second leg distal end 32 and the second leg proximal end 34. The first leg length and the second leg length are independently adjustable. This can be useful to orientate the lead askew or at an angle during operation of the lead insertion tool 10.

FIG. 5 is a perspective view of an illustrative lead insertion tool 10 of FIG. 4 gripping a paddle lead 60. FIG. 6 is a perspective view of an illustrative lead insertion tool 10 of FIG. 4 mated to a rear portion 66 of the paddle lead 60 for pushing the paddle lead. These figures illustrate a method of using the illustrative lead insertion tool 10.

The illustrative paddle lead 60 includes opposing top and bottom major surfaces 62, 64 joined together by opposing lateral side surfaces 61, 63 and a front edge surface 65 and a rear edge surface 66. The channel 28, 38 of the rails 25, 35 mate with the opposing lateral side surfaces 61, 63 of the paddle lead 60. Conductors or leads or lead extensions 68 extend from the rear edge surface 66 of the illustrative paddle lead 60.

This method includes gripping a paddle lead 60 along opposing lateral edges 61, 63 with opposing rail elements 25, 35 of a lead insertion tool 10. The opposing channels 28, 38 of the rail elements 25, 35 mate with the opposing lateral side surfaces 61, 63 of the paddle lead 60. The opposing rails 25, 35 form an angle with the first and second legs 20, 30 as described above. The opposing rails 25, 35 include an optional slot 29, 39 extending into a distal end of each rail, as described above.

The method includes placing the paddle lead 60 into an initial target area and releasing the paddle lead 60 from the lead insertion tool 10. Then the method includes contacting the rail elements 25, 35 together to form a slot 29, 39 configured to receive the paddle lead 60. The slot 29, 39 can mate with and receive the rear edge surface 66 of the paddle lead 60. Once the proximal end 66 of the paddle lead 60 is engaged into the slot 29, 39, the paddle lead 60 can be pushed into a second target area with the lead insertion tool 10.

In many embodiments the lead insertion tool first and second legs are not coupled to each other and can be provided as a medical kit or assembly or system that may or may not include the lead to be inserted. In these embodiments the first and second legs are fixed to forceps 400 as an extension of each leg of the forceps. In many of these embodiments the rail element is not pivotally coupled to the tool leg, as illustrated in FIG. 7A and FIG. 8A. In some embodiments, the rail element is pivotally coupled to the tool leg, as described above.

FIG. 7A is a perspective view of another illustrative lead insertion tool 200 that can be secured to forceps 400. FIG. 7B is a perspective view of an illustrative lead insertion tool 200 of FIG. 7A gripping a paddle lead 60. The paddle lead 60 is described above. One useful aspect of this embodiment is that the illustrative lead insertion tool 200 can be used once and discarded, thus eliminating the need to sterilize the illustrative lead insertion tool 200 after use.

The illustrated lead insertion tool 200 has a first leg 220 and a second leg 230 forming sleeves to receive the opposing leg elements 420, 430 of the forceps 400. A set screw 223, 233 can be utilized to fix the opposing leg elements 420, 430 of the forceps 400 onto the first leg 220 and a second leg 230.

This lead insertion tool 200 includes a first leg 220 having a first leg distal end 222 and an opposing first leg proximal end 224. A first rail element 25 is fixed to the first leg distal end 222. In other embodiments the first rail element 25 is pivotally coupled as described above. A second leg 230 has a second leg distal end 232 and an opposing second leg proximal end 234. The second leg 230 can be parallel extending with the first leg 220. A second rail element 35 is fixed to the second leg distal end 232. In other embodiments the second rail element 35 is pivotally coupled as described above. The first rail element 25 and the second rail element 35 are configured to receive a lead and can include a channel 28, 38 that can mate with and receive a surface of a lead body, such as a paddle lead, as described above.

The first rail element 25 and the first leg 220 form an angle θ as described above. In some embodiments where the first rail element 25 and the first leg 220 are pivotally coupled, the intersection of the first rail element 25 and the first leg 220 includes detent elements that create a plurality of pre-set angles θ, as described above. In many embodiments the first rail element 25 and the first leg distal end 222 form a smooth angle, as described above. The first leg 220 is fixed to an opposing leg 420 of a forceps device 400. Once the procedure is complete the first leg 220 is removed from the opposing leg 420 of a forceps device 400 and either discarded or sanitized for use.

The first rail element 25 is described in relation to FIG. 1-6 above. The first rail element 25 can include a channel 28 that extends along its length. The channel 28 can be configured to mate with and receive a surface of a lead. For example, the channel 28 can be configured to mate with and receive a side surface of a paddle lead as illustrated in FIG. 7B to locate the lead in a target area.

The second rail element 35 and the second leg 230 form an angle θ as described above. In some embodiments where the second rail element 35 and the second leg 230 are pivotally coupled, the intersection of the second rail element 35 and the second leg 230 includes detent elements that create a plurality of pre-set angles θ. In many embodiments the second rail element 35 and the second leg distal end 232 form a smooth angle, as described above. The second leg 230 is fixed to an opposing leg 430 of a forceps device 400. Once the procedure is complete the second leg 230 is removed from the opposing leg 430 of a forceps device 400 and either discarded or sanitized for use.

The second rail element 35 is described in relation to FIG. 1-6 above. The second rail element 35 can include a channel 38 that extends along its length. The channel 38 can be configured to mate with and receive a surface of a lead. For example, the channel 38 can be configured to mate with and receive a side surface of a paddle lead as illustrated in FIG. 7B to locate the lead in a target area.

The rails 25, 35 can include a slot 29, 39 configured to receive a lead, especially when the first and second rails 25, 35 are in contact with each other. The slot 29, 38 extends into the rail distal end. In many embodiments the slot 29, 39 is coextensive with the channel 28, 38 and extends along a length of the rail 25, 35. The slot 29, 39 can be configured to mate with and receive a surface of a lead. For example, the slot 29, 39 can be configured to mate with and receive an end surface of a paddle lead as illustrated in FIG. 6 to push the lead into a final target area.

FIG. 8A is a perspective view of another illustrative lead insertion tool 300 that can be secured to forceps 400. FIG. 8B is a perspective view of an illustrative lead insertion tool 300 of FIG. 8A gripping a paddle lead 60. The paddle lead 60 is described above. One useful aspect of this embodiment is that the illustrative lead insertion tool 300 can be used once and discarded, thus eliminating the need to sterilize the illustrative lead insertion tool 300 after use.

The illustrated lead insertion tool 300 has a first leg 320 and a second leg 330 that include two or more cuff elements 370, 380 to receive the opposing leg elements 420, 430 of the forceps 400. Detent elements can be aligned with the cuff element 370, 380 to an fix the opposing leg elements 420, 430 of the forceps 400 onto the first leg 320 and a second leg 330.

This lead insertion tool 300 includes a first leg 320 having a first leg distal end 322 and an opposing first leg proximal end 324. A first rail element 25 is fixed to the first leg distal end 322. In other embodiments the first rail element 25 is pivotally coupled as described above. A second leg 330 has a second leg distal end 332 and an opposing second leg proximal end 334. The second leg 330 can be parallel extending with the first leg 320. A second rail element 35 is fixed to the second leg distal end 332. In other embodiments the second rail element 35 is pivotally coupled as described above. The first rail element 25 and the second rail element 35 are configured to receive a lead and can include a channel 28, 38 that can mate with and receive a surface of a lead body, such as a paddle lead.

The first rail element 25 and the first leg 320 form an angle θ as described above. In some embodiments where the first rail element 25 and the first leg 320 are pivotally coupled, the intersection of the first rail element 25 and the first leg 320 includes detent elements that create a plurality of pre-set angles θ. In many embodiments the first rail element 25 and the first leg distal end 322 form a smooth angle, as described above. The first leg 320 is fixed to an opposing leg 420 of a forceps device 400. Once the procedure is complete the first leg 320 is removed from the opposing leg 420 of a forceps device 400 and either discarded or sanitized for use.

The first rail element 25 is described in relation to FIG. 1-6 above. The first rail element 25 can include a channel 28 that extends along its length. The channel 28 can be configured to mate with and receive a surface of a lead. For example, the channel 28 can be configured to mate with and receive a side surface of a paddle lead as illustrated in FIG. 8B to locate the lead in a target area.

The second rail element 35 and the second leg 330 form an angle θ as described above. In some embodiments where the second rail element 35 and the second leg 330 are pivotally coupled, the intersection of the second rail element 35 and the second leg 330 includes detent elements that create a plurality of pre-set angles θ. In many embodiments the second rail element 35 and the second leg distal end 332 form a smooth angle, as described above. The second leg 330 is fixed to an opposing leg 430 of a forceps device 400. Once the procedure is complete the second leg 330 is removed from the opposing leg 430 of a forceps device 400 and either discarded or sanitized for use.

The second rail element 35 is described in relation to FIG. 1-6 above. The second rail element 35 can include a channel 38 that extends along its length. The channel 38 can be configured to mate with and receive a surface of a lead. For example, the channel 38 can be configured to mate with and receive a side surface of a paddle lead as illustrated in FIG. 8B to locate the lead in a target area.

The rails 25, 35 can include a slot 29, 39 configured to receive a lead, especially when the first and second rails 25, 35 are in contact with each other. The slot 29, 38 extends into the rail distal end. In many embodiments the slot 29, 39 is coextensive with the channel 28, 38 and extends along a length of the rail 25, 35. The slot 29, 39 can be configured to mate with and receive a surface of a lead. For example, the slot 29, 39 can be configured to mate with and receive an end surface of a paddle lead as illustrated in FIG. 6 to push the lead into a final target area.

Thus, embodiments of the LEAD INSERTION TOOL are disclosed. All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A lead insertion tool comprising:
   a first leg having a first leg distal end and an opposing first leg proximal end, a first rail element is pivotally coupled to the first leg distal end; and
   a second leg having a second leg distal end and an opposing second leg proximal end and parallel extending with the first leg, a second rail element is pivotally coupled to the second leg distal end, wherein the first rail element and the second rail element are configured to receive a lead,
   wherein each of the first rail element and the second rail element extends between a rail distal end and an opposing rail proximal end along a longitudinal direction to define a rail lateral length, wherein the rail proximal end of the first rail element is pivotally coupled to the first leg distal end and the rail proximal end of the second rail element is pivotally coupled to the second leg distal end,
   wherein the rail distal ends of the first and second rail elements together define a slot, wherein the slot comprises an aperture extending entirely through the first and second rail elements in a lateral direction orthogonal to the longitudinal direction, wherein the slot is configured to receive a lead extending through the aperture to push the lead in the longitudinal direction, and
   wherein the first leg has a first leg length extending between the first leg distal end and the first leg proximal end and the second leg has a second leg length extending between the second leg distal end and the second leg proximal end and the first leg length and the second leg length are independently adjustable.

2. The lead insertion tool according to claim 1, wherein the first leg is coupled to the second leg at the first leg proximal end and second leg proximal end.

3. The lead insertion tool according to claim 1, wherein the first leg is not coupled to the second leg.

4. The lead insertion tool according to claim 1, wherein the slots each extend into the distal end of the respective rail element.

5. The lead insertion tool according to claim 1, wherein the proximal end of the first rail element and the first leg distal end form a smooth angle.

6. The lead insertion tool according to claim 3, wherein the first leg and the second leg are configured to affix to forceps.

7. A lead insertion tool comprising:
a first leg having a first leg distal end and an opposing first leg proximal end, a first rail element is pivotally coupled to the first leg distal end; and
a second leg having a second leg distal end and an opposing second leg proximal end and parallel extending with the first leg, a second rail element is pivotally coupled to the second leg distal end, the first rail element and the second rail element are configured to receive a lead,
wherein each of the first leg distal end and the second leg distal end comprises a plurality of detent elements that define a plurality of pre-set angles formed by the pivotally coupled first rail element and pivotally coupled second rail element.

8. The lead insertion tool according to claim 7, wherein the first leg has a first leg length extending between the first leg distal end and the first leg proximal end and the second leg has a second leg length extending between the second leg distal end and the second leg proximal end and the first leg length and the second leg length are independently adjustable.

9. The lead insertion tool of claim 7, wherein the rail distal ends of the first and second rail elements together define a slot, wherein the slot comprises an aperture extending entirely through the first and second rail elements in a lateral direction orthogonal to the longitudinal direction, wherein the slot is configured to receive a lead extending through the aperture to push the lead in the longitudinal direction.

10. The lead insertion tool according to claim 7, wherein the first leg and the second leg are configured to affix to forceps.

11. The lead insertion tool according to claim 7, wherein each of the first rail element and the second rail element has a rail distal end and an opposing rail proximal end and the rail proximal end of the first rail element is coupled to the first distal end and the rail proximal end of the second rail element is coupled to the second leg distal.

12. The lead insertion tool according to claim 9, wherein the slot is configured to receive the lead when the first and second rail elements are in contact with each other.

13. The lead insertion tool according to claim 7, wherein a pre-set angle formed by the first rail element coupled to the first leg distal end is a smooth angle.

14. A medical kit comprising:
a lead insertion tool according to claim 7; and
a paddle lead that is configured to be received by the first rail element and second rail element.

15. The medical kit according to claim 7, wherein the first leg is coupled to the second leg at the first leg proximal end and second leg proximal end.

16. The lead insertion tool according to claim 7, wherein each of the first and second rail elements comprises a channel configured to receive a surface of the lead.

17. The lead insertion tool according to claim 16, wherein the channels of the first and second rail elements are configured to receive opposing lateral side surfaces of the lead.

18. The lead insertion tool according to claim 16, wherein each of the channels of the first and second rail elements extends along a length of the respective rail element.

19. The lead insertion tool according to claim 7, wherein each of the first and second rail elements comprises a slot extending into a distal end of the respective rail element and is optionally coextensive with the respective channel.

20. The lead insertion tool according to claim 19, wherein the slots are configured to mate and receive the lead to push the lead into a target area.

\* \* \* \* \*